US00PP24848P2

(12) United States Plant Patent
Egger

(10) Patent No.: US PP24,848 P2
(45) Date of Patent: Sep. 2, 2014

(54) ***SEDUM* PLANT NAMED 'DESERT RED'**

(50) Latin Name: *Sedum telephium (Hylotelephium telephium)*
Varietal Denomination: Desert Red

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 62 days.

(21) Appl. No.: 13/815,314

(22) Filed: Feb. 19, 2013

(51) Int. Cl.
*A01H 5/00* (2006.01)

(52) U.S. Cl.
USPC ..... Plt./479

(58) Field of Classification Search
USPC ..... Plt./479
See application file for complete search history.

*Primary Examiner* — Annette Para
(74) *Attorney, Agent, or Firm* — Klarquist Sparkman, LLP

(57) ABSTRACT

A new and distinct hybrid of *Sedum* plant substantially as shown and described, characterized by a low flat, habit with multiple stems from the crown and from branching, narrow leaves that are gray brown with dark edges in the spring and deep brown in the summer, rose red flowers in numerous clusters, bright red seed heads, extending the showy season, and excellent vigor.

2 Drawing Sheets

Botanical denomination: *Sedum telephium* (*Hylotelephium telephium*).

Variety designation: 'Desert Red'.

BACKGROUND OF THE INVENTION

The present invention relates to a new and distinct cultivar of *Sedum telephium* and given the cultivar name of 'Desert Red'. *Sedum* is in the family Crassulaceae. *Sedum* 'Desert Red' originated from an open pollinated cross of *Sedum telephium* 33-14, a proprietary, unpatented plant.

Compared to *Sedum telephium* 33-14, the new cultivar has a smaller, denser habit with darker, narrower leaves.

Compared to *Sedum* 'Picolette', an unpatented plant, the new cultivar is shorter and wider spreading with more stems from the base, the foliage and stems are darker, and the flowers are a darker pink.

Compared to *Sedum* SUNSPARKLER™ 'Dazzleberry', an unpatented plant, the new cultivar has darker leaves and stems, rose red flowers rather than rose pink, and bright red seed heads rather than brown.

SUMMARY OF THE INVENTION

This new and unique *Sedum* is distinguished by:

1. a low flat, habit with multiple stems from the crown and from branching,
2. narrow leaves that are gray brown with dark edges in the spring and deep brown in the summer,
3. rose red flowers in numerous clusters,
4. bright red seed heads, extending the showy season, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 2 shows the same plant with the red seed heads in October.

FIG. 3 shows the spring leaves of the same plant, the previous May.

DETAILED PLANT DESCRIPTION

Figure 1:
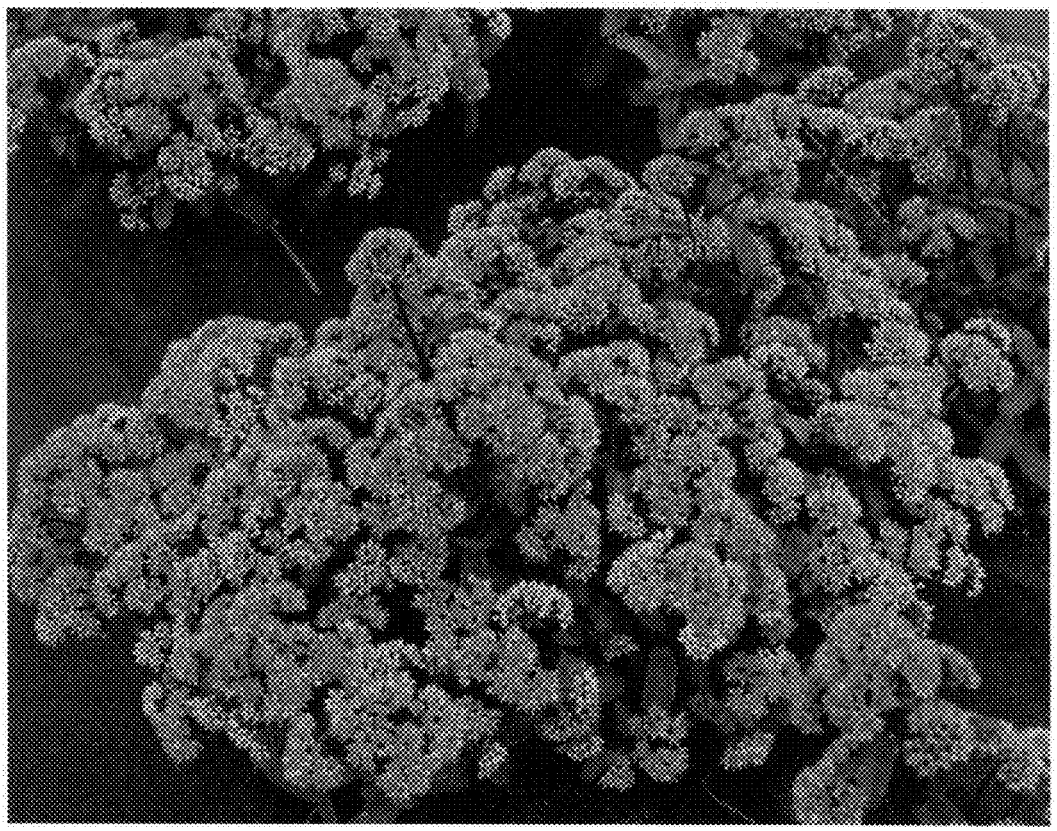
FIG. 1 shows a one-year-old *Sedum* 'Desert Red' growing in the trial fields just starting to flower in late August in Canby, Oreg.

The following is a detailed description of the new *Sedum* hybrid based on observations of two-year-old specimens grown in the trial field in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:

*Type*.—Herbaceous perennial.
*Hardiness*.—USDA Zone 4 to 9.
*Size*.—22 cm tall and 52 cm wide.
*Habit*.—Mat forming clumping.
*Vigor*.—Excellent.

Stem:

*Number*.—About 18.
*Size*.—23 cm long and 10 mm wide.
*Internode length*.—0.5 mm to 4 mm long.

*Color*.—Greyed Purple N186A in sun and Greyed Green 191A in full shade, except at base where closest to Grey Brown 199B.
*Texture*.—Succulent.
*Surface*.—Glabrous.

Leaf:
*Type*.—Simple.
*Arrangement*.—Variable, mostly opposite.
*Shape*.—Oblanceolate.
*Apex*.—Obtuse.
*Base*.—Cuneate.
*Venation*.—Pinnate.
*Margins*.—Sometimes serrate.
*Blade size*.—Grows to 4.5 cm long and 1.7 cm wide.
*Surface*.—Glaucous.
*Texture*.—Succulent.
*Petiole*.—Leaves sessile.
*Leaf color*.—Spring topside between Greyed Green N189B and 191A with the main vein Greyed Green 191C on top and bottom side, leaf margins Greyed Purple N187A, bottom side closest to Greyed Green 191C tinted Greyed Purple N187A in the sun; summer topside Brown 200A including veins; bottom side closest to Greyed Green 191A including veins.

Inflorescence:
*Type*.—Terminal, corymbose.
*Number of flowers*.—Over a 1000 per stem (the number of flowers/stem increases with age).
*Pedicels*.—1 mm to 3 mm long, 1 mm wide, glabrous, Grey Brown N199A.
*Peduncle*.—3 cm to 9 cm tall and grows to 5 mm wide, Greyed Purple N186A in sun and Greyed Green 191A in full shade, succulent, glabrous.
*Size*.—Grows to 9 cm deep and 10.5 cm wide.
*Bloom period*.—Late August through September in Canby, Oreg.

Flower bud:
*Size*.—2 mm wide, 4 mm deep.
*Description*.—Ovoid.
*Color*.—Red Purple 65D.

Flower:
*Type*.—Incomplete, actinomorphic.
*Shape*.—Stellate.
*Size*.—4 mm deep and 6 mm wide.
*Corolla description*.—3 mm deep and 6 mm wide, 5 petals, each lanceolate, 4 mm long and 1.5 mm wide, margins entire, tip acuminate, glabrous on both sides, both sides Red Purple 65A on the tip and blending to Red Purple 65D at the base.
*Calyx description*.—1.5 mm deep and 2.5 mm wide, stellate, 5 lobes, divided to the base, margins entire, tip acute, glabrous, Grey Brown N199A on both sides.
*Pistil description*.—5 separate prominent showy carpels, each 4 mm deep and 1.5 mm wide, Red Purple 59B; style 1 mm long and Red Purple 59A; stigma Red Purple 59A.
*Stamen description*.—None, no pollen, male sterile.
*Fragrance*.—None.
*Lastingness*.—Each stem lasts about a month.

Fruit:
*Type*.—Ventrally dehiscent follicle, erect, attenuate.
*Fertility*.—Low.
*Color*.—Red 42A.

Seed: Black.

Disease and pest resistance: Pest and disease resistance are typical for this type of *Sedum*. No known resistances.

I claim:

1. A new and distinct hybrid of *Sedum* plant as herein illustrated and described.

* * * * *

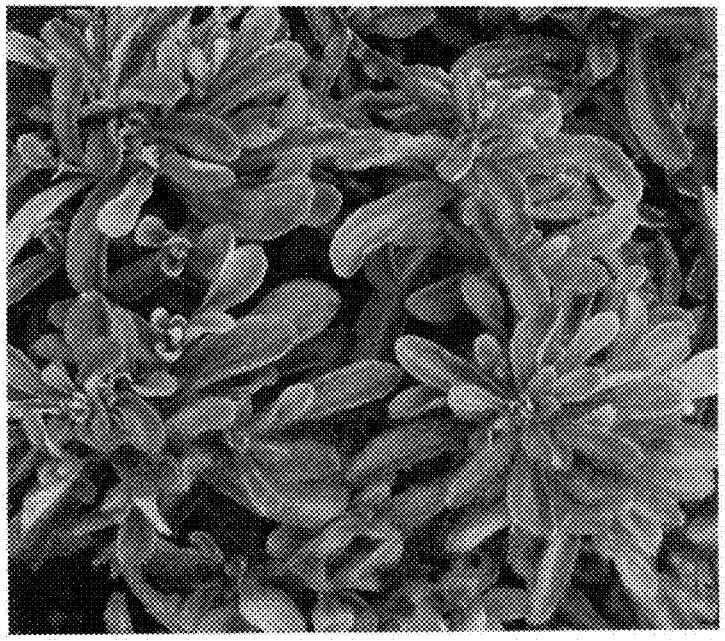

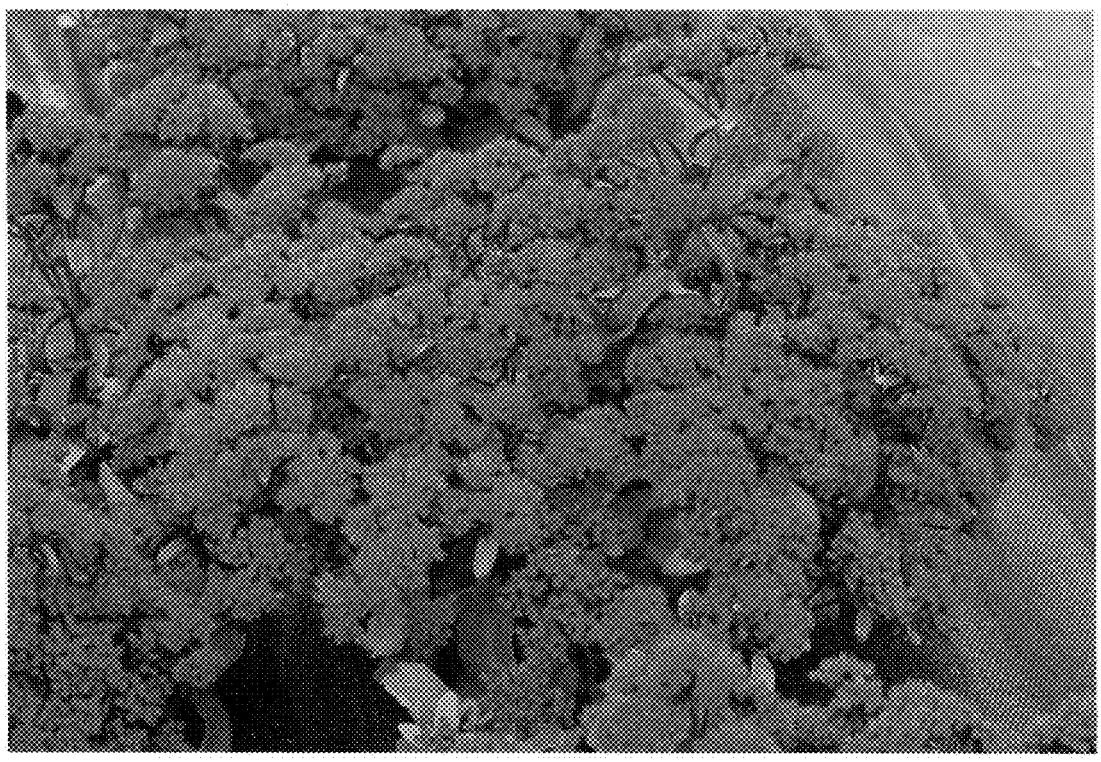
FIG. 2 above, FIG. 3 below